United States Patent [19]

Fitzmorris et al.

[11] Patent Number: 4,691,231

[45] Date of Patent: Sep. 1, 1987

[54] BOTTLE INSPECTION SYSTEM

[75] Inventors: Tyce Fitzmorris; Eric Espenhahn, both of Lake Park; Jamie Pereira, North Palm Beach, all of Fla.

[73] Assignee: Vistech Corporation, Lake Park, Fla.

[21] Appl. No.: 782,432

[22] Filed: Oct. 1, 1985

[51] Int. Cl.[4] .................. H04N 7/18; G01N 9/04; G01N 21/16; B07C 5/00

[52] U.S. Cl. .................. 358/106; 358/107; 250/223 B; 356/240; 209/522; 209/526; 209/939

[58] Field of Search ............. 358/106, 107; 356/428, 356/240; 250/223 B; 209/522, 524, 526, 939

[56] References Cited

U.S. PATENT DOCUMENTS

| | | | |
|---|---|---|---|
| 3,439,178 | 4/1969 | Rottmann | 250/222 |
| 3,708,680 | 1/1973 | Calhoun | 250/223 B |
| 3,721,501 | 3/1973 | Atkinson et al. | 356/201 |
| 3,746,784 | 7/1973 | van Oosterhaut | 358/106 |
| 3,747,755 | 7/1973 | Senturia et al. | 209/111.5 |
| 3,778,617 | 12/1973 | Calhoun | 250/223 B |
| 3,886,356 | 5/1975 | Gomm et al. | 250/223 B |
| 3,932,042 | 1/1976 | Faani et al. | 250/223 B |
| 3,956,629 | 5/1976 | Gomm et al. | 250/223 R |
| 4,002,823 | 1/1977 | van Oosterhaut | 358/106 |
| 4,047,000 | 9/1977 | Bryant et al. | 250/223 B |
| 4,136,930 | 1/1979 | Gomm et al. | 358/106 |
| 4,170,417 | 10/1979 | Tourres | 250/223 B |
| 4,172,524 | 10/1979 | Holm et al. | 209/524 |
| 4,259,571 | 3/1981 | Dubberly | 250/223 B |
| 4,280,624 | 7/1981 | Ford | 209/524 |
| 4,376,951 | 3/1983 | Miyazawa | 358/106 |
| 4,378,494 | 3/1983 | Miller | 250/223 B |
| 4,403,858 | 9/1983 | Yoshida | 250/223 B |
| 4,414,566 | 11/1983 | Peyton et al. | 358/101 |
| 4,428,674 | 1/1984 | Giebel et al. | 250/223 B |
| 4,459,487 | 7/1984 | Leser | 250/223 B |
| 4,487,322 | 12/1984 | Juvinall | 356/240 |
| 4,492,476 | 1/1985 | Miyazawa | 250/223 B |
| 4,500,203 | 2/1985 | Bieringer | 250/223 B |
| 4,509,081 | 4/1985 | Peyton et al. | 358/106 |
| 4,579,227 | 4/1986 | Miller | 358/106 |
| 4,601,395 | 7/1986 | Juvinall et al. | 358/106 |
| 4,636,635 | 1/1987 | Krönseder | 356/240 |

*Primary Examiner*—Tommy P. Chin
*Assistant Examiner*—Michael D. Parker
*Attorney, Agent, or Firm*—Steele, Gould & Fried

[57] ABSTRACT

A method and apparatus for inspecting the sidewalls of containers on a continuously-moving conveyor includes recording instantaneous upper and lower angularly-spaced images of the bottles as they pass. Data on the images is stored as numeric data indicating the grey shade of each pixel in a matrix of pixels, which matrix is examined for edges and then divided based on detected edges into inspection windows. The windows are subject to separate criteria between typically scuffed areas and open areas. The occurrence of pixels in at least three grey ranges reflecting clear glass, opaque glass, and scuffed glass, together with the correlation of such occurrences between angularly-spaced views and upper and lower views, is processed to detect defects. A memory stores a status indication in a queue representing the acceptability of the bottles being examined, which are then segregated by a downstream reject kicker mechanism.

20 Claims, 12 Drawing Figures

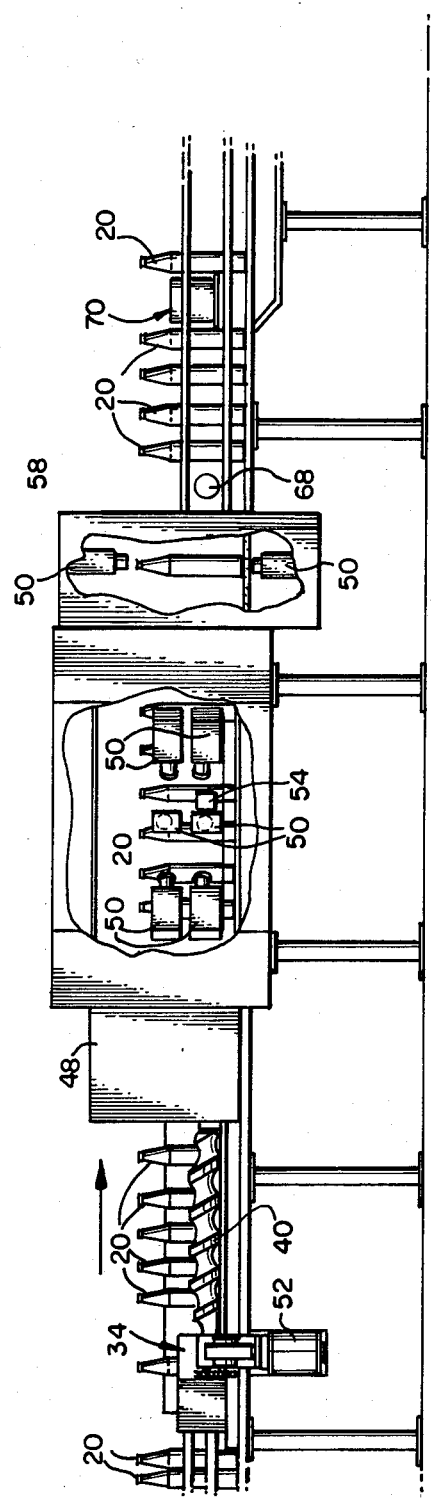
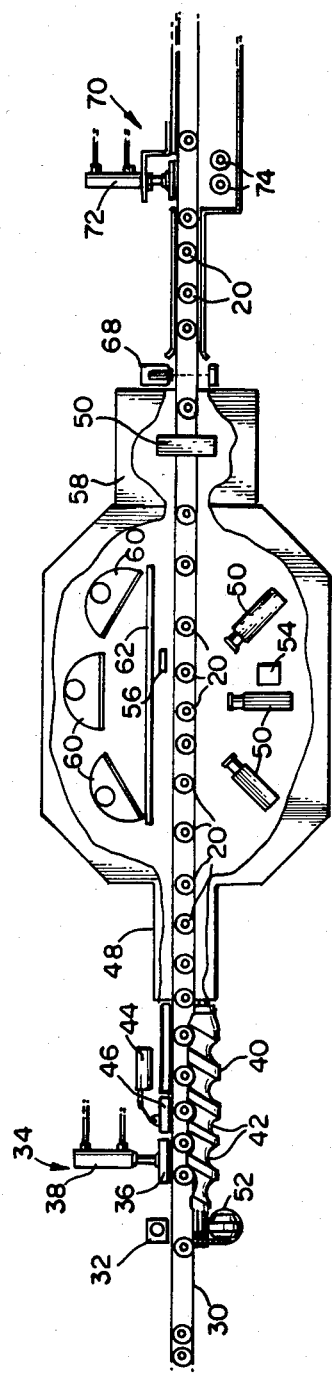

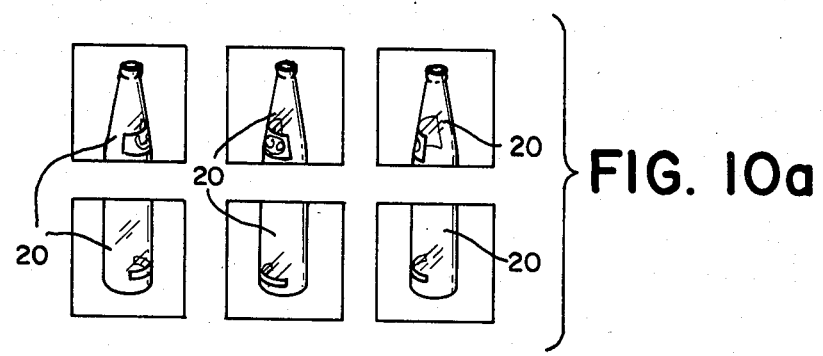
FIG. 10a
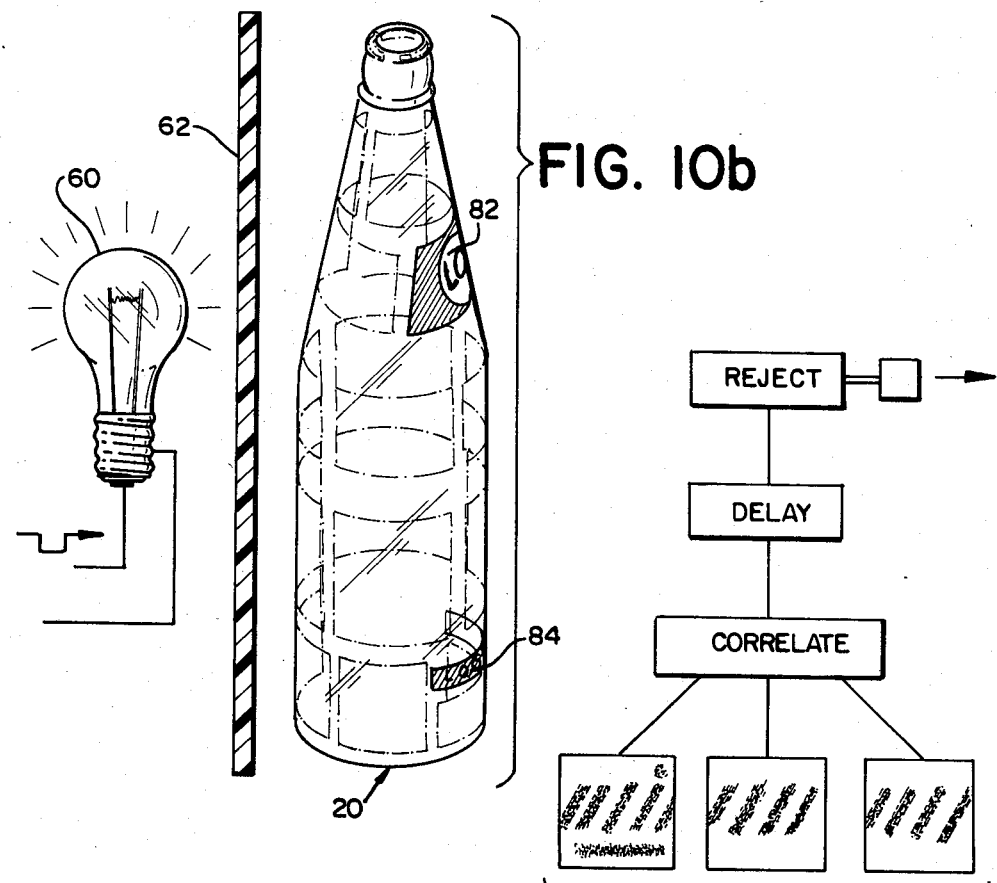
FIG. 10b
FIG. 10c

BOTTLE INSPECTION SYSTEM

BACKGROUND OF THE INVENTION

1. Field of the Invention

This invention relates to the field of automated inspection systems, and in particular to an inspection and selection device for examining transparent or translucent returnable glass bottles and the like, selection being based upon the detection of optical patterns, for example indicating dirt, foreign material on or in the glass, proper filling of full bottles, or breakage. According to the invention selection is also based on the extent of scuffing, for detection of excess bottle wear.

2. Prior Art

A wide variety of bottle inspection systems are known in the art, including systems intended to inspect the top lip, bottom or sidewalls of bottles and hollow containers. Sidewall inspection is shown, for example, in U.S. Pat. Nos. 3,439,178—Rottmann; 3,886,356—Gomm, et al.; 3,932,042—Faani, et al.; 4,136,930—Gomm, et al.; 4,170,417—Tourres; 4,172,524—Holm, et al.; 4,280,624—Ford; 4,376,951—Miyazawa; 4,378,494—Miller; and 4,414,566—Peyton, et al. The methods and apparatus disclosed in these patents include the use of plural cameras and video processing. Various light sensing and signal processing techniques are used in efforts to detect everything from cracks to movable foreign material suspended in filled bottles. Nevertheless, even in view of this wide variety of disclosures, the one and only type of automated bottle inspection system that is sufficiently cost-effective and reliable for general use in the industry today is the type of system that inspects only the cap-receiving lips and possibly also the bases of bottles.

Known base and/or lip-examining devices are effective and practical, probably because the procedure for detection of defects and the type of defects are much less complicated than in sidewall inspection. The lip and base can be readily examined in plan view. At least the lip portion, which is carefully dimensioned to begin with in order to sealably receive a cap, must have no defect at all. Defects in the base or lip portion that justify rejection, specifically chips and cracks, are typically gross defects that are readily detectable. Unlike inspection of bases and lips, inspection of sidewalls requires examining for progressive wear as well as for gross defects. Bottle inspection devices to date have been too expensive or unable to exercise the necessary judgment for inspection of all bottle areas, lip, bottom and sidewall, which has until now required a human inspector.

In bottle inspection systems, video signal processing is used as a means to detect occurrences of contrasting light and dark in a bottle sidewall. The references mentioned above include devices which use the light and dark indication to sense the edge of bottles, and also to sense the presence of defects, which appear as contrasting dark spots on a light background, and sudden level changes in a video signal. Such systems can detect opaque defects and cracks in the lip or base, and also at least in the center of view of a sidewall. Unfortunately, even if the views are optically enlarged an/or multiplied by rotating the bottle or the like, such defects are not the only problem in sidewall-inspection systems.

In the case of returnable glass bottles such as soft drink bottles, beer bottles, and the like, after a number of cycles through bottling and use, the handling of the bottle causes damage in the form of scuffed or abraded surfaces of the bottle. The typical bottles are conical on an upper half and generally cylindrical on a lower half, the cusp between the conical and cylindrical part defining an exposed contact area against which the bottle is abraded in regular expected handling. Similar damage is expected on the lower-most edge of the bottle. These scuffing areas become more and more clouded (i.e. relatively more diffuse) as a bottle wears. At some point, the extent of scuffing becomes unacceptable; but until then, a scuffed bottle is still acceptable for reuse. A human inspector will exercise judgment in gauging the degree of bottle wear. In an automated system to detect wear, the simple detection of scuffing is not enough to achieve accuracy of selection comparable to a human inspection.

Other defects occur in bottles that are such that a human will miss. These should also be detected, but they do not show up in a video signal as a simple dark spot or the like. These include the presence of residual water remaining in a bottle after cleaning, the presence of trapped crumpled cellophane (e.g. clear cellophane from a cigarette wrapper) and the like. Problems with detecting these defects are aggravated by other defects or potential defects such as scuffing, and are also aggravated if the detection system is to be used with rippled or colored translucent bottles such as green or brown-colored bottles, as well as with clear ones.

Prior art systems have been unduly expensive. Moreover, although effective in detecting discrete attributes such as opaque spots and cracks, known inspection systems have not been effective with segregating for continuously-varying progressive defects and potential defects such as scuffing. Furthermore, the mechanical complication of inspection systems that has heretofore been required to account for even such variations as the alignment of the bottle label, differences in bottle dimensions and problems with positioning, have made prior art devices impractical for general use except for limited examination of lips and bases.

The present invention incorporates known lip and base inspection techniques, but has overcome many of the defects of prior art sidewall inspection systems by using a plurality of cameras and one or more associated video processors to separately examine upper and lower areas of the bottle from angularly-spaced views. Edge detection (i.e., contrast detection) techniques are used to define inspection windows in the views that expand the inspection area to the maximum but exclude edges and label areas, regardless of the bottle orientation. Views are backlighted and are angularly spaced more than 180 degrees such that centrally-located inspection windows in the video image, viewing through both the opposite sidewalls of the container, expose substantially all the defects present.

Separate selection standards are applied for a given bottle to normally-scuffed areas and open inspection areas, selection being based upon not only opacities, but also correlation of features in the regions and upon statistical analysis of the light and dark levels of the individual pixels in the image. Preferably, six video cameras are used for sidewalls, three for angularly-spaced elevation views at two levels and each providing, for example, a 256×240 matrix of pixels. The gray level at each of the pixels is detected to one of 256 separate levels of light to dark. Strobe lights or momentarily-opened camera shutters are used freeze the image of each of the moving bottles for inspection without mechanically stopping them. Preferably, sequential frozen frames of the bottle are recorded as it moves along continuously. The video cameras can be angularly spaced around the bottle, or linearly spaced along the bottle conveyor and combined with a means for turning the bottle disposed between the stations. Even given suppressing data adjacent the bottle edges in each view, the cameras provide useful data at a high angle of incidence to the bottle surfaces for the lip, base and substantially the entire circumference. Notwithstanding the substantial resolution of the video system, statistical examination of the pixel gray levels, together with correlation of the results for different areas, provides an effective bottle inspection device of modest expense.

The lack of general application of bottle sidewall inspection systems to bottling operations has been due to considerations of both effectiveness and expense. The expense to be considered is more than monetary. Currently, bottling plants use human inspectors to examine bottles moving continuously along a conveyor at speeds up to 250 bottles per minute. This job is boring, difficult and dangerous in that so many bottles stream past the inspector's fixed gaze and the view of the bottles is so hypnotizing that it shortly becomes impossible to detect even the relatively small proportion of bottles which have gross defects such as chips and opaque areas. One inspector may last only 20 minutes until relieved. Even a fresh inspector has no real hope of detecting subtleties.

Full-time human staffing of an inspection job represents an overhead expense that is not justifiable if at least comparable selection success can be obtained automatically. Furthermore, the proximity of the human inspector to the stream of fast-moving bottles is downright dangerous, as the bottles are often impelled against one another and sometimes shatter from thermal cycling from the upstream hot water and steam washing apparatus. Nevertheless, in the prior art, systems have not been available which could dependably exercise the judgment regarding progressive defects such as scuffing of bottle surfaces necessary to remove bad bottles from the good.

SUMMARY OF THE INVENTION

It is an object of the invention to provide an inexpensive and effective bottle inspection apparatus that is sensitive to both defects of high contrast and defects characterized by subtle differences between bottles and/or a variable range of deterioration.

It is also an object of the invention to provide a bottle inspection system that can be installed on a conveyor operating at full bottling speed, without unnecessary mechanical interference with the bottles, and without undue necessity of handling or alignment of bottles.

It is yet another object of the invention to provide a bottle inspection system that is insensitive to the presence of dirt and vibration, and insensitive to variations in bottle types, orientation and conveyor speed, yet has sufficient resolution and processing speed to accurately discriminate between fine variations in bottles.

It is still another object of the invention to provide an inspection system characterized by maximum selection accuracy, minimum expense and minimum interference with bottling functions.

These and other objects are accomplished by a method and apparatus for inspecting the sidewalls of containers on a continuously-moving conveyor including sequentially freezing upper and lower images of the bottles at views spaced around the bottle's circumference as they pass. Data on the images is stored as numeric data indicating the gray shade of each pixel in a matrix of pixels, which matrix is examined for edges and then divided into inspection windows. The data patterns of the windows are separately handled to discriminate scuffed areas from open areas and to ignore opaque labels. The occurrence of pixels in at least three gray ranges reflecting clear glass, opaque glass, and scuffed glass, together with the correlation of such occurrences between angularly-spaced views and upper and lower views, is processed to detect defects. Detection and selection for lip and base defects in upper and lower plan view may be concurrently carried out. A memory stores a status indication in a queue representing the acceptability of the bottles being examined, which are then segregated by a downstream reject kicker mechanism.

BRIEF DESCRIPTION OF THE DRAWINGS

There is shown in the drawings the embodiments which are presently preferred. It should be understood that the invention is not limited to the precise arrangements and instrumentalities shown, and furthermore, that the invention is subject to various combinations of features which may be shown separately in the drawings for purposes of illustration.

FIG. 1 is an elevation view of a bottle inspection system according to the invention, the casing around the inspection zone being shown partly cut away.

FIG. 2 is a top plan view of the device, the top of the casing shown removed.

FIGS. 10a, 10b and 10c are schematic illustrations of selective window definition and processing.

DETAILED DESCRIPTION OF THE PREFERRED EMBODIMENTS

Figure 3:
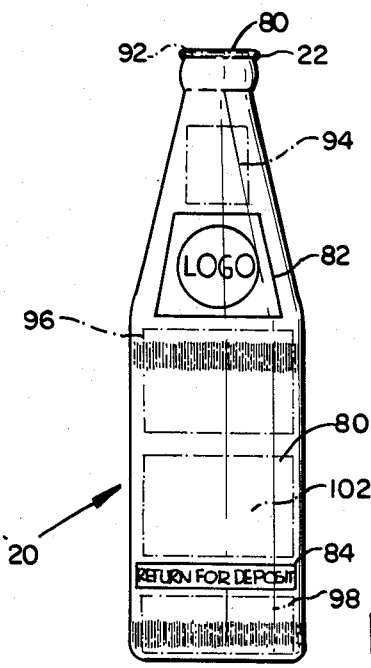
FIG. 3 is an elevation view showing the bottle to be inspected, inspection windows being shown in broken lines.

FIGS. 1 and 2 illustrate a first embodiment of the invention, wherein the video cameras 50 are provided at two heights and are angularly spaced around a bottle arriving at an inspection station along a conveyor. Bottles 20, which are moving from left to right in FIGS. 1 and 2 along conveyor 30, are closely spaced or touching as they arrive at gate mechanism 34. In order to allow an unobstructed view of each bottle around an angular space, in this embodiment the bottles 20 are separated from one another by a short distance, using separator auger screw 40. Auger 40 is essentially a large screw driven by motor 52 and having an increasing outer diameter and decreasing pitch in the conveying direction such that the bottles are carried along in the areas of lowest diameter on auger 40, being released into the inspection enclosure at a slight space from one another, at least the width of a bottle.

The inspection enclosure can be bounded by cowlings 48, at both the entry and exit portions of the conveyor, which cowlings keep out spurious light which might produce reflections or shadowing. Alternatively, one cowling 48 can be provided on the input side, and at the output side this function is served by a top/bottom inspection device 58, for example also including cameras 50, as shown in FIGS. 1 and 2.

The conveyor moves continuously. Preferably, the section of conveyor including the inspection enclosure is provided with a constant speed conveyor, moving at a rate at least equal to the fastest speed to be expected in the conveyor mechanism (not shown) that delivers bottles to the inspection device. It is contemplated that the inspection device will be placed downstream of the cleaning operation in a bottling plant, and upstream if the filling equipment such that clear, clean, empty bottles are examined for defects in or on the glass. Other inspections, for example, the fill level or the character of bottle contents, are also possible, perhaps using a plurality of inspection systems.

Bottles arriving at the inspection system, spaced by auger 40, are detected when they are approximately centrally located in an inspection zone. At the point when the bottles are in direct view of the cameras, they break a beam from photo cell 54. Photo cell 54, including an associated light source and a light detector, is directed towards reflector 56 on an opposite side of the conveyor path such that the beam crosses the conveyor path. A leading edge of a bottle entering the zone interrupts the beam, producing a change in resistance in the cell, which is amplified to produce a pulse for initiating an inspection operation.

In general, the inspection operation involves recording six different video scan fields of the bottle from different views. The fields are then analyzed and inspection areas ("windows") are defined. The fields can show the bottle by back lighting with a diffuse light source, whereupon opacities show dark. The bottle can also be shown at least partly by front lighting, which allows discrimination based on light and dark reflective attributes. The light source(s) preferably include strobe lights 60, located behind diffuse light transmitting element 62, the latter being immediately behind the bottle to be back lighted. Constant light sources and camera shutter arrangements can also be used. The views each show relatively clear areas representing the central front and back thicknesses of glass, and gray to black shades representing the foreshortened sides of the round bottle.

Frozen video scan fields could be recorded simultaneously for multiple views using a single strobe light. For purposes of processing time, it is preferred that the six cameras be operated in pairs sequentially, synchronized with operation of one of three opposed strobe lights, and that dual processors share the load of analysis.

The six cameras are provided at three locations, and at two elevations at each location, laid out to produce views at different areas around the bottle. The upper cameras are served by a first video processor and the lower cameras are served by another. Operation of the video cameras, video processors and strobe lights are also synchronized such that upon arrival of a bottle at the inspection zone, the strobe light fires precisely at the beginning of recording of the next video. The order of firing of the strobe lights is not critical, provided the associated video camera is operated at the same time, to record the scanned field synchronously with firing of each strobe light. A triggered flash lamp may be adapted to maintain illumination during the scanning of horizontal lines in recording a single video image. Preferably, however, the instantaneous condition of illumination during a much-shorter strobe period of illumination (e.g., a five hundredth of a second) is recorded or latched at once and then read out from the video camera at the usual video scanning speed.

The three pairs of video cameras may be angularly spaced by 60 degrees from one another and aimed at substantially the same zone, each viewing through the two opposite sides of the bottle against the back lighted diffuse illumination barrier 62. This produces views from different angles around the bottle. A similar result is obtained by aligning the cameras parallel, at a space from one another along the conveyor, and interspersing means for turning the bottles between the cameras. Preferably, diffuse barrier 62 is located very close to the bottle being inspected, which helps to provide a clear view through both the front and back bottle walls. Of course, inasmuch as the bottle is circular in section, the central portion of the view, i.e., diametrically through the bottle walls along a line perpendicular to their surfaces, appears lightest in color. Portions adjacent the edges appear progressively darker due to the viewing along a tangent to the surface, through a greater width of glass. Variations in distance from the barrier 62 also affect shading of the image. Any surface features on the bottle will be foreshortened and darker approaching the edges. Features are most clear when seen in the center of the view. By spacing the video cameras to record scan fields 60 degrees around the bottle from one another, each viewing nearly 180 degrees, a greater than 180 degree view of the bottle is obtained. It is then possible to ignore features in the difficult to view areas adjacent the edges. Nevertheless, the central portions of the images taken diametrically through the opposite sidewalls of the bottle, when taken together comprise all or nearly all the circumference of the bottle.

A video camera suitable for use with the present invention is the solid-state black-and-white TV camera model KP-120 sold by Hitachi Denshi, Ltd., 175 Crossways Park, West, Woodbury, N.Y. 11797. Each camera is preferably provided with a 16 mm wide angle lens, positioned approximately 16 inches from the bottles being inspected. Although it may be possible to use a wider angle lens at a closer spacing or to use longer focal length optics at a greater spacing, considerations of distortion, compactness and expense are balanced such that the six camera system, with 16 mm lens and 16 inch spacing is preferred to achieve good quality upper and lower views at three references angularly-spaced around the bottle.

The sidewall inspection of the system is also capable of embodiment using fewer cameras than six and fewer processors than two. For example, one processor and three cameras will produce similar results if the cameras are of sufficient resolution and the processor is sufficiently fast. It would also be possible to use more cameras and processors in a suitable application.

Video processing of the signals for a given bottle is accomplished as the bottle continues to move along the conveyor to be replaced by another bottle. Preferably the inspection is completed at the maximum speed expected for the production line as a whole. However, inasmuch as the bottles may be initially separated as in the embodiment of FIGS. 1 and 2, the conveyor in the inspection area may be required to run faster than the overall production line.

A line control mechanism including a memory storage queue for storing the pass/fail status of bottles moving along the line between the inspection area and the downstream conveyor, keeps a count of bottles inspected and bottles passing an outlet photo cell 68. Each time a bottle passes outlet photo cell 68, the memory queue is advanced by one. If the passing bottle is a rejected bottle, a delay is initiated, after which delay the kicker mechanism 70, for example including a controllable air cylinder 72 and a movable contact member, physically segregate the rejects from the remaining bottles by urging rejects 74 off the conveyor to a catch area or other conveyor.

A typical bottle being inspected is shown in elevation in FIG. 3. The bottle is generally cylindrical along its lower portion and generally conical at it upper portion, terminating in a round lip 22 adapted to receive a cap (not shown). Lip 22 is very-precisely formed, and must be completely free of defects in order to sealably interact with a cap, normally a metal cap threaded or crimped over lip 22. Of course consumers drinking from the bottle place lip 22 against their own lips. Any defects such as chip 80 could injure the consumer and could also prevent an air-tight seal. Any single such defect in lip 22 of even minimal size should be detected as grounds for rejecting the bottle.

The upper or conical section of the bottle frequently includes an opaque painted-on label 82, for example including the trademark. Although it might be useful to detect dirt or damage occurring behind the opaque label, this is often not possible using visible light. According to the invention, the bottle may be front lighted as well as back lighted to enable a certain examination of the label area. The edges of label 82 are also used as one of the means defining the placement of the clear glass inspection windows, which are applied to the remaining portions of the bottle.

Should a bottle fall over on its side, the sidewalls and especially the portion of the bottle at the cusp between the conical upper portion and the cylindrical lower portion are exposed to damage. This cusp area frequently is noticeably abraded in used bottles. This area of abrasion may be termed a "scuff" or "scratch". Usually, the damage is not structurally threatening to the bottle, but if the abrasion is extreme, for cosmetic reasons and also because unknown defects may be concealed, the bottle should be rejected.

The appearance of the abraded area on the bottle in the video signal thereof is a diffusely darker or cloudy band in that area. A similar band normally occurs at the bottom edge of the bottle sidewalls, which is another area which is exposed to contact and abrasion during automatic machinery processing or rough bottle handling and use. In the usual case, if a bottle has been used enough that noticeable abrasion has occurred, the scuffing or abrasion at the lower most edge of the bottle has progressed further than similar abrasion around the central band. Therefore, one may expect some good bottles havin no abrasion, detectable abrasion adjacent the base, or detectable abrasion in both bands. However, should diffuseness typical of abrasion be found in the central band and not the lower band, the detected diffuseness is likely to be caused by some phenomena other than scuffing. In that event, the bottles should probably be rejected on the ground that that the detected diffuseness reflects, for example, a crumpled piece of cellophane in the bottle, residual water on inner surfaces or other defects. These defects are not readily distinguishable from abrasion by simply comparing the gray shade. According to the invention, gray shade occurrences in individual windows.

The video cameras produce an analog representing luminance in the scanned image. The signal is sampled and digitized to produce a succession of numeric values representing the shade of gray at the corresponding spot in the view. In video processing the digitized signals, which is undertaken in times between recording views of passing bottles, a first step is to find the edge of the bottle in the video signal such that the darker foreshortened edges of the bottle are not considered for defects, at least in that view. The label position (if any) is also found. It may be possible to sufficiently-precisely position the photo cell 54 and its reflector 56, together with the position and orientation of cameras 50, that the bottle will appear at the same relative position in the view for every camera and every bottle inspected. It may also be possible to orient the labels prior to processing. These possibilities are not practical. In order to avoid the necessity for careful alignment, and in order to allow as great an inspection window area as possible, the inspection windows for the bottle are defined for each passing bottle, based upon detection of a pattern in the data representing at least one edge, for example a side, label or bottom. The upper and lower boundaries of windows adjacent printed labels on the bottle being defined by edge detection techniques for each bottle, the upper or lower termination of a video inspection window can be expanded as much as permitted by whatever labels happen to be present.

A suitable video processing computer for use with the invention is marketed by International Robomation/Intelligence, 2281 Las Palmas Drive, Carlsbad, CA 92008, as model IRI P256. Two of these processors are preferably provided, each with an autonomous operating system that acquire image data upon occurrence of a pulse at an input for processing at the user's option. Two video processor computers are preferred to avoid processing speed problems. A first processor serves the upper three angularly-spaced video cameras and a second processor serves the lower three. A single faster processor or a single processor operating on lower data resolution could also be used, the one processor serving three or six cameras. The processor may also service one or two further cameras for top and base inspection.

Processing may be conducted independently and asynchronously for the defined inspection windows and different view for the two systems, except that in order to finally judge the acceptability of a piece that is characterized by diffuseness that may indicate scuffing, the results achieved by the individual computers for the respective inspection windows must be correlated for different angles and for the two elevations. In particular, should diffuseness such as that caused by scuffing be detected by one of the angularly spaced cameras and not by others viewing the bottle from other angles, the scuffing is interpreted as dirt and the bottle is rejected. Should a scuffed band be found at the central cusp area and not the bottom edge area, the scuff band is likewise suspicious, and the bottle should be rejected. Such correlation of results allows a certain amount of judgment whereby different types of possible flaws can be identified.

Detection of an opaque spot of greater than predetermined size may be detected as a reject fault. Preferably, fault detection is based upon the number of proportion of lighter and/or darker pixels rather than their proximity to one another, and upon the overall shade of the bottle as defined by the number of occurrences of pixels in certain shades. This statistical selection technique is quite effective.

The IRI P256 Vision System is based upon a Motorola 68000 micro processor, and the system is adapted to automatically handle the acquisition of pixel information, and the storage thereof in a portion of random access memory dedicated to video memory. The video data processors as configured preferably have a user-programmed random access memory of 64K thirty-two bit words and video memory including four fields of 64K bytes of video data, each byte including 8 bits, and each byte being therefore capable of recording a gray level to a resolution of one part in 256.

Referring to FIG. 3, which shows defined inspection windows in broken lines, edge detection specifically is accomplished by choosing one or more horizontal lines in the video image and comparing the pixel data for successive pixels in the chosen row or rows. Should an area of consistent contrast be found, for example 5-10 pixels in a row showing a contrast of ten gray count levels over a previous 5-10, then an edge is considered found. The defined edge of an inspection window is then displaced backwards from the detected edge by an amount tending to restrict the size of the windows but to suppress contrasting parts of the complete image, especially the dark edges of the bottle as viewed along a substantially foreshortened surface and through relatively thicker portions of glass. In FIG. 3, edge detection is used for example to define right and top edges for a "lip" window 92, an upper part "clear space" window 94, and upper "scratch window" 96, a lower "clear space" window 102, and a bottom edge "scratch window" 98. In these cases, the "clear" spaces are meant to refer to views through the front and back walls that are spaced inward slightly from the foreshortened edges. The "scratch" windows are like clear ones except the scratch windows are those of areas of typical abrasion damage. The edges for each of these windows may be determined independently, or it may be possible to determine one or both opposite edges of one of the windows, in each view, for example clear space windows 94, 102 and to define the edge of the other window in that view by relative displacement of a predetermined number of pixels from the edge detected for windows 94, 102.

Upper and lower edges are determined in a similar manner by examining pixel data for contrast in columns. The upper edge of the bottle defines the upper edge of lip window 92. The edges of label 82 define the lower edge of upper clear window 94 and the upper edge of scuff window 96. The label does not always appear in the views. The label will not be seen, for example, with a no-label bottle or upon certain angles of incidence for a labelled bottle. Therefore, the spacing between windows 94, 96 can be made variable to depend upon the detection of the label. In a bottle with no label or in a side view in which the label is not seen, windows 94, 96 can be expanded to a maximum, and even abut directly against one another. Similar processing around the lower edge of the bottle and the edges of a lower label 84 is likewise employed to provide the largest possible inspection window without overlapping the label 84.

Figure 4:
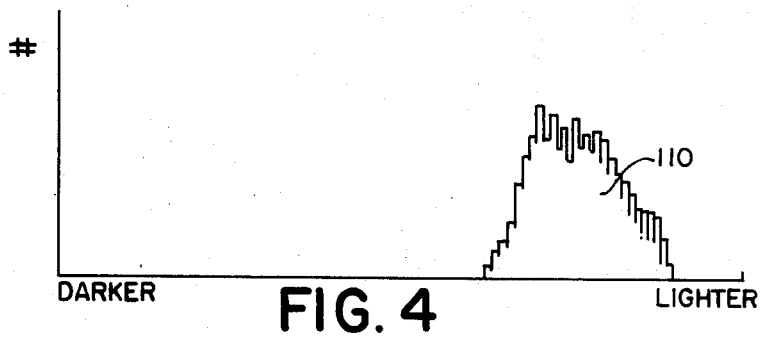
FIG. 4 is a histogram illustrating a typical clear window.

The video data processors are adapted to develop a count of occurrences of gray lavel pixels (i.e., a histogram) for each inspection window under test. It is possible to develop a histogram based on all the pixels, to a resolution of one grey level. It is also possible to treat pixels and or gray levels in groups or to skip pixels in order to decrease data processing time for statistical analysis. For example, if every other pixel is counted to develop a histogram, or the average of every two adjacent pixels is used for the histogram, resolution remains good. Shortcuts such as these can be used to develop criteria for selection (i.e., setpoints) that are related to the specific bottle being tested, which criteria can then be applied to all the available data and not only the shortcut data. Example histograms are shown in FIGS. 4 and 5.

Clear space windows 94, 102, present the normally least-obstructed of the views through the bottle against the diffuse background member 62. These areas may be expected to exhibit the least variation in gray color. However, inasmuch as the bottle is round, the foreshortening of the surface at the outer edges and the fact that more glass is placed between the camera and the background adjacent the outer edges than across the diameter, causes a variation in gray level that is clearly detectable even for "clear" windows. Accordingly, the distribution of colors even at these relatively-unobstructed windows 94, 102, will follow a certain distribution of gray shades. With reference to FIG. 4, a typical distribution is a smooth bell curve. The mean of this curve may vary, for example reflecting bottle color or due to accumulation of dust on the cameras or slow dimming of the strobe light intensity over time. The standard deviation (i.e., the relative width of the bell) is more constant and can be used to determine whether a good sample has been taken.

Figure 5:
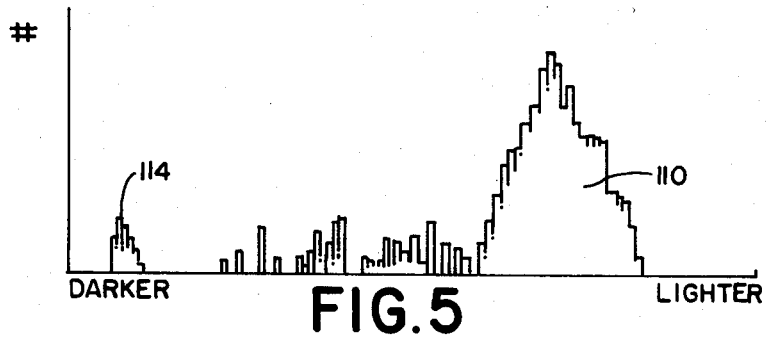
FIG. 5 is a histogram characteristic of a bottle having certain defects.

Referring to FIG. 5, a distribution indicative of possible defects is characterized by a distribution other than a smooth bell, and especially by the occurrence of dark pixels 114. Dark pixels indicate opacity, e.g., dirt which was not removed during cleaning. A distribution of intermediate gray tones 112, approaching the dark may also mean dirt. The intermediate gray tones 112 might also reflect the existence of scuffing. Occurrences of dark elements and/or opaque features on the bottle, such as dirt spot 80, shown in FIG. 3, are counted. If these are too numerous they are cause to reject.

Figure 6:
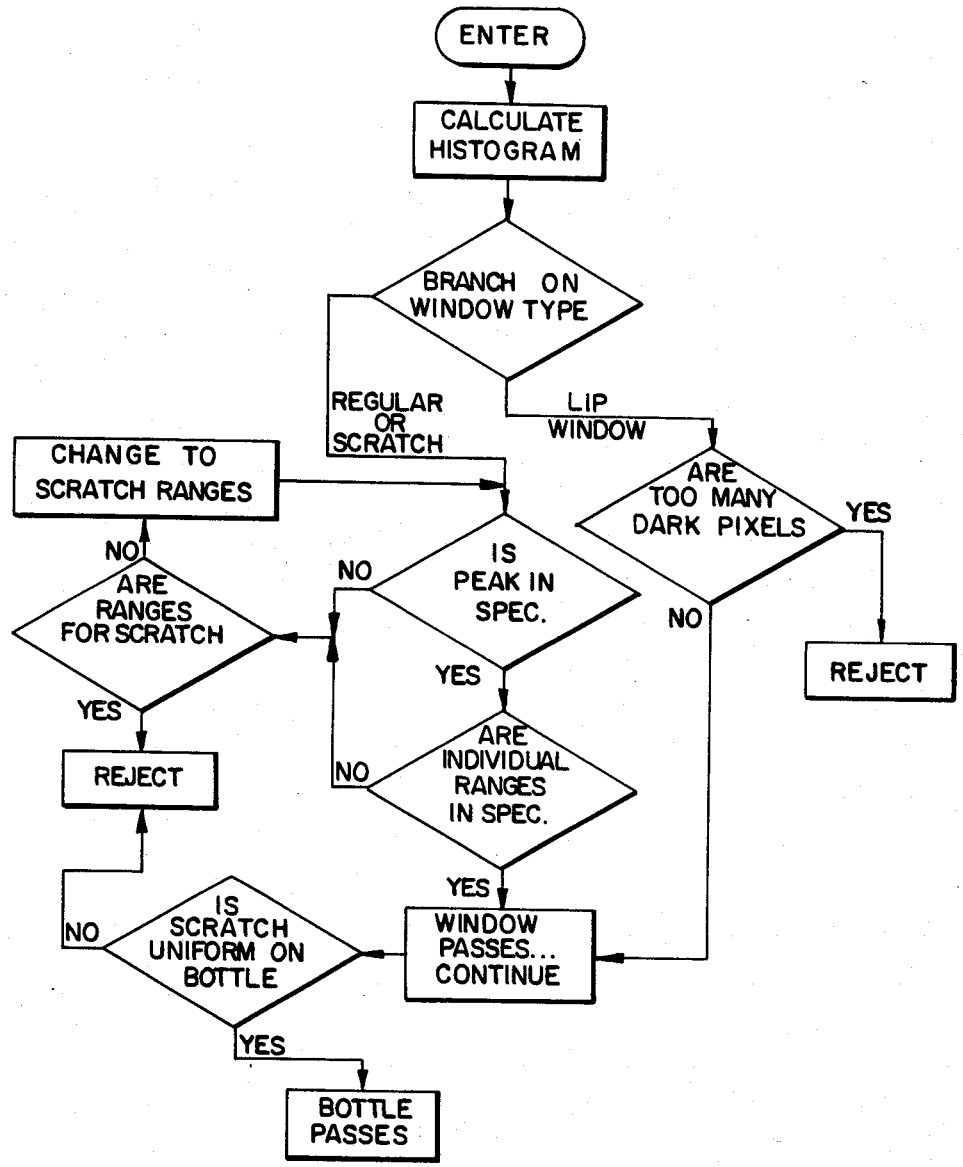
FIG. 6 is a flow chart showing a preferred sequence of analysis steps applied to the video representation of individual images and window therein.

In processing the histogram data developed from individual inspection windows, a sequence is followed as represented in FIG. 6. Different processing sequences are conducted for the individual inspection windows based upon which type of inspection window is under consideration. If a scratch window is under consideration, i.e, central window 96 or lower window 98, the bell curve of the histogram is first examined, to determine whether the peak is within the range of acceptable limits. A peak outside of limits may indicate a problem with video image recordation or processing such as a misplaced trigger from photocell 54, misalignment of the inspection window (e.g. from erroneous edge detection due to a vertical scratch), or some other reason why the process has not gone as expected. Although the peak is considered an adequate means for determining whether a meaningful sample has been taken, other attributes of the sample, for example the standard deviation, may also be checked against predetermined standards.

If the peak is within specifications (maximum and minimum predetermined levels) for either a scratch window 96, 98 or a regular window 94, 102, then the number of occurrences in subdivided gray level ranges within the overall range of light to dark in the histogram are also checked. If both the peak and the number of occurrences within individual ranges are within the predetermined maximum and minimum number of occurrences, the bottle is considered to have no defects at this inspection window. Should either the peak or the number of occurrences in any of the individual ranges be out of programmed limit for a regular window 94, 102, then the bottle is rejected on the ground that dirt or damage has been detected.

For scuff or scratched windows 96, 98 more-lenient number-of-occurrence limits are applied for the ranges when scuffing is detected than if the bottle is found to be unscuffed. In that event, however, other criteria are applied to distinguish good bottles from bad, based upon both the extent of diffuseness (i.e, the number of occurrences of mid-range gray pixels) and the uniformity thereof from window to window around the bottle and in the upper and lower views.

First, possibly-scratched or scuffed bottles are identified. Upon detection of a peak or number of occurrences within individual gray ranges that do not meet the maximum/minimum criteria for a regular window, then the bottle window is suspect. Provided the suspect window is a scratch window, the allowed ranges for the bottle scratch windows are expanded to lenient scratch standards. If the scratch window does not pass the lenient specifications, the bottle is rejected.

If the lenient scratch specifications are passed, the remaining angular views of any bottle already identified as scratched must also be found to have similar characteristics. In this way, the uniformity of scratching is checked to ensure that it is in fact scratching that has been detected and not some other progressively-varying features such as residual water, cellophane or the lie, which have a different characteristic video signature than scratching. The analysis therefore exercises a certain "judgment" as a human inspector would exercise, instead of blindly applying set standards to all bottles and all areas thereof.

The checking of the lip window is somewhat less complicated than the other windows in that characteristic damage ot the lip (e.g., chips), is much more discrete and produces a more identifiable signature than progressive damage such as scuffing. Furthermore, virtually any departure from perfection in a lip is cause to reject. Therefore, the lip window is effectively checked by simply testing whether the number of dark pixels in the dark ranges exceeds a maximum permitted.

The lips and bases of the passing bottles are preferably examined in plan view to detect defects. A top-and-bottom inspection device 46 as known in the art can be incorporated with the sidewall inspector of the invention, the pass/fail indication for the top and bottom being logically-OR'ed with that of the sidewall inspector. Such a system is shown in FIG. 11.

The subranges within the light and dark ranges for sidewall (or top/bottom) windows under examination can be chosen in several ways. It is possible to simply define ranges of the gray levels experimentally found to be indicative of clear glass, progressive or diffuse damage (e.g., scuffing) and opaque damage. It is also possible to define additional ranges such that the device can be discern between colored glass and clear glass, and even between glasses of different colors such as green vs. brown. It is presently preferred that the ranges be determined for a bottle under test with reference to the peak of the histogram found for an inspection window. The full gray range is subdivided into useful ranges by dividing the space between the peak of the histogram and the known darkest pixel shade into at least three groups representing (at least) clear glass, scuffed glass and opaque material. A further range to the lighter side of the peak would represent reflections and refractions from trapped cellophane or reflections from front-lighted defects. Defining the ranges based on actual occurrences makes processing automatically self-calibrating and not subject to undue deterioration due to accumulation of dust, progressive dimming of the strobes, etc.

As noted above, in the event a bottle is identified as an apparently scratched bottle due to detection of diffuseness in one of the six scratch window areas, and assuming the extent of scratching is within limits considered acceptable for the window, the placement and uniformity of scratching are also relevant to acceptability. In order to distinguish a video signature representing scratching from an otherwise similar signature representing, for example, trapped cellophane, residual water, or other defects, scratched bottles must be found to be uniformly affected. Normally, dirt in the bottles appears as opaque and is detectable as occurrence of very-dark range pixels. Cracks and chips in the bottles likewise produce at least some very-dark pixels within the inspection windows. However, cellophane, residual water, partly-diluted syrup spots and scuffing are characterized by a more spread-out distribution. Of these, only scuffing can be expected to be uniform as between the different angular views and as expected in extent between the upper and lower scratching zones.

The inspection system according to the invention is preferably made self-diagnostic. Ongoing monitoring of the number of detections of defects or scuffing features is carried on such that the occurrence of an unusual selection rate can be used to generate an alarm and/or to stop processing. It is expected that in a typical return-for-deposit bottling plant, upwards of 80 percent of the bottles will be within specifications and not scuffed. 15–20 percent will be scuffed and acceptable even if marginal. The remainder are the expected rejects. Should rejects not meet the expected rates, for example a maximum 5 percent and minimum 1 percent of the total, or should scuffing exceed 20 percent or be less than 5 percent, then the operation of the system is suspect. It is possible that either or both of the two video processors output a "fault" signal in the event that expected selection rate are not realized.

Preferably, a line control device is connected to both processors, the line controller handling both reporting functions and the generation of fault indications for unexpected selection rates. The line controller can include reporting features such as display of current process variables, and can be used to house the upper-/lower correlation, reject queue and delay functions as well (see FIG. 10c). A fault signal from any of the line controller, the two processors and the top/bottom inspector can be used to operate the air cylinder to close the gate mechanism 34 at the entry to the inspection device, which gate mechanism can also be closed upon faults detected in other areas of the system, such as downstream jamming, a fallen bottle or the like.

Figure 7:
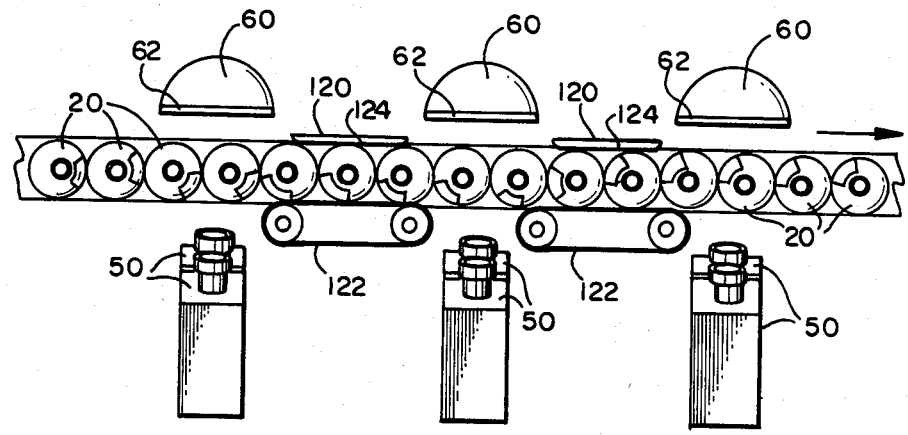
FIG. 7 is an elevation view of an alternative bottle inspection zone.

Processing speed according to the invention can be substantially increased by use of an alternative embodiment of the system that allows the bottles to be processed without being initially separated from one another. In the previously-discussed embodiment comprising bottle-separating auger 40, the video cameras were angularly spaced around the bottle and aimed radially inward at the inspection zone. The bottles were initially spaced such that the outer cameras would have an unobstructed view of the bottle sidewall along an angle inclined with respect to the conveyor. In the embodiment shown in FIG. 7, the bottles are processed when resting directly against one another, the inspection zone being divided into three areas and the bottles being physically turned 120 degrees between the areas. This arrangement is functionally similar to the angularly-spaced arrangement but the cameras are spaced and are aimed in parallel at different inspection zones. In either case, views are provided of angularly spaced locations around the bottle's circumference. Moreover, in the embodiment of FIG. 7, the bottle can be turned more than by 60 degrees from view to view such that all portions of the bottle are viewed from both the front and back sides. Preferably the bottle is turned by 120 degrees per increment.

As in the foregoing embodiments, two video cameras are provided for upper and lower views of the bottle, respectively. The bottle arriving at the first station is examined by the first pair of cameras in the random angular orientation at which it arrives. Between the first and second station, a bottle turning mechanism 120 is provided along the conveyor between the first station and the next. At the bottle turning mechanism 120, the bottle is urged against a non-moving stop 124 on one side of the conveyor, by means of a rolling stop 122 disposed on the opposite side. The rolling stop can be driven, for example at the speed of the conveyor, by a motor or gearing connection (not shown). Both sides of conveyor can have rolling stops driven in opposite directions. The stops are resilient and are spaced just less than the bottle diameter. The effect is to roll the bottle. By dimensioning the length of the turning mechanism to achieve a 120 degree turn, the bottle arrives at the second station with a different face presented for inspection by the second pair of cameras. A similar bottle turning mechanism 120 is disposed between the second and third stations, completing the process.

If bottles must be spaced prior to inspection, the inspection conveyor must move faster than other parts of the production line, to account for the gaps between bottles. The device of FIG. 7 can process bottles at a speed equal to production line conveyor speed, because there is no need to separate the bottles. Similarly, handling of the bottles, but for the twisting between the stations, is unnecessary.

In all, both embodiments of the system of the invention avoid any unnecessary handling of the bottles and, insofar as possible, examine the bottles by non-contact techniques and with a minimum of bottle handling and mechanical devices. Therefore, less breakage can be expected, and greater human safety will be realized. The lack of direct contact with the bottles and handling also results in an overall cleaner inspection system that is remarkably more effective than any known systems currently available.

Figure 8:
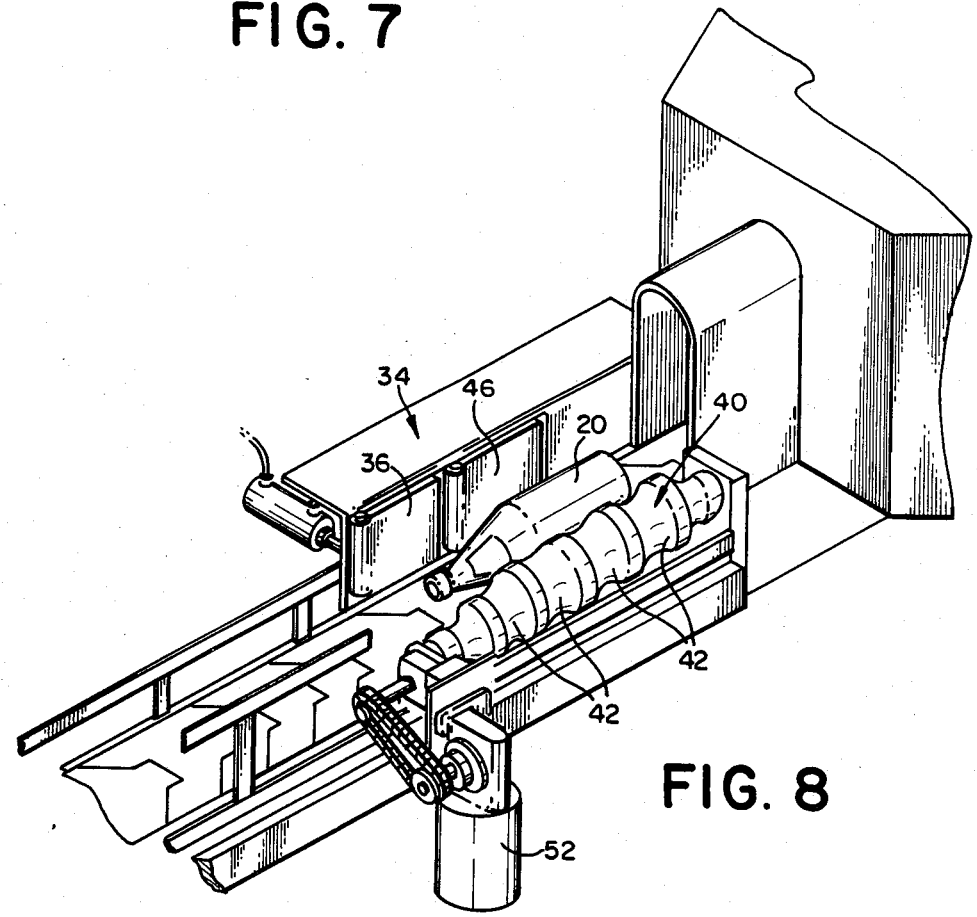
FIG. 8 is a perspective view illustrating a bottle jam at the intake of the inspection device.

Although handling of the bottles is minimized, it is possible that a bottle will arrive in a mis-aligned condition at the input to the conveyor. As noted above regarding FIG. 2, a gate mechanism 34 is provided at the input to the inspection device, whereby successive bottles can be blocked from entry upon detection of a fault. The stop device 34 comprises a stop plate under control of the line-control circuitry and responsive to fault detections by the processors and/or by the line control circuitry itself. Gate 34 simply restricts the width of the conveyor such that oncoming bottles cannot pass, and are not picked up by the spacing auger 40. Auger 40 is designed with an increasing outer diameter and a decreasing pitch, in order to engage and spearate the bottles. The increase in outer diameter along the auger is meant to gently urge the bottles into the depressions 42 as the bottles advance and auger 40 turns under influence of auger motor 52. Should a bottle arrive horizontally, as shown in FIG. 8, the increasing diameter of auger 40 tends to urge the bottle against the sidewall, and particularly against the jam-detector plate 46, pivotally attached along the side of the conveyor. The bottle is forced to one side of the conveyor because its horizontal alignment prevents its resting in depressions 42, and the increasing diameter of the auger therefore urges it against plate 46. Behind plate 46 is a limit switch, shown in FIG. 2, by which jam detection is accomplished. Limit switch 42 is adapted to generate a 'fault' indication and cause extension of the stop plate 36. Preferably operation of the gate also activates an alarm which will bring manual assistance to relieve the jam or other fault.

Figure 9:
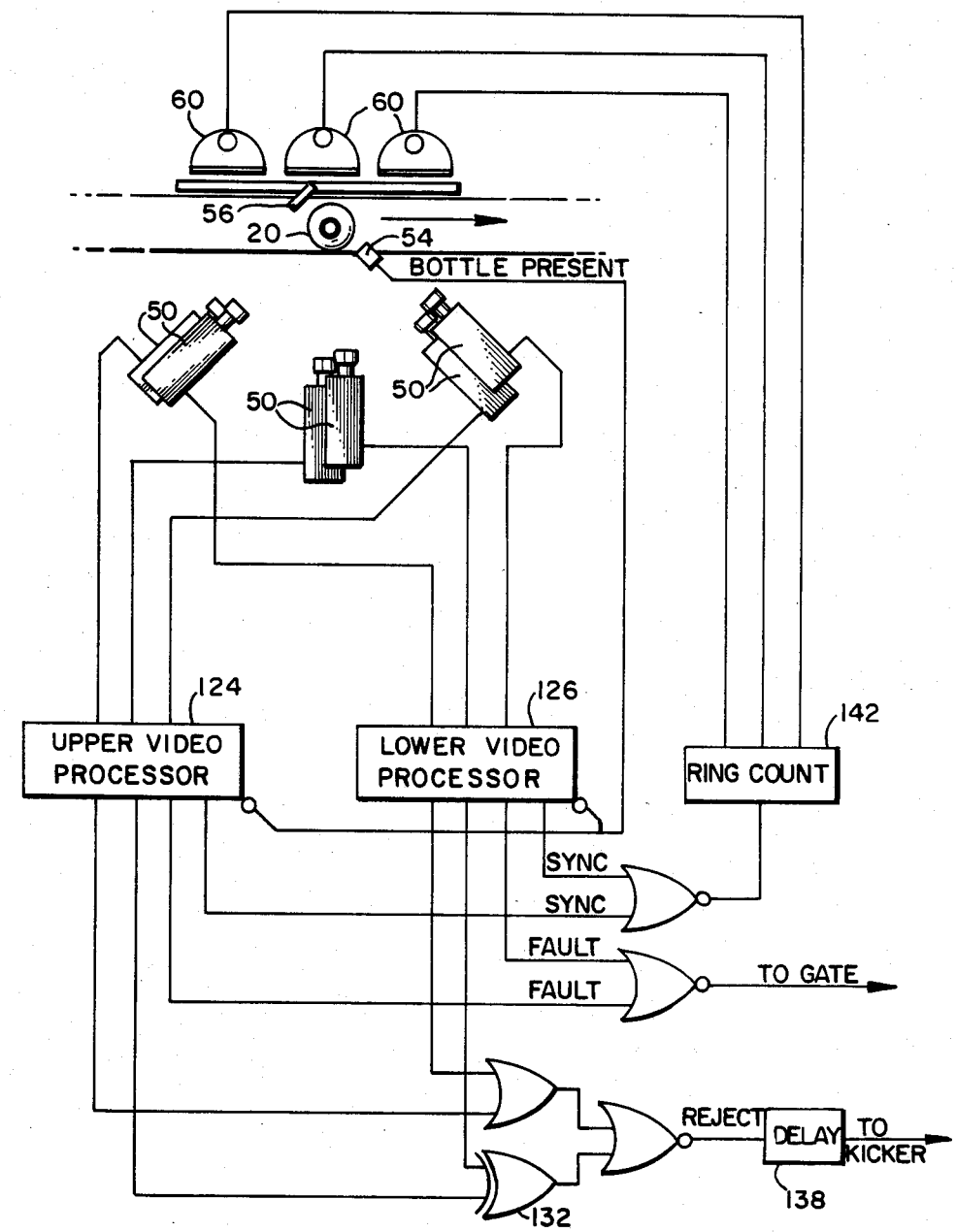
FIG. 9 is a schematic logic diagram showing interconnection of inspection and line control elements.

A schematic illustration of the circuitry of the invention is shown in FIG. 9. As discussed hereinabove, the upper three video cameras are serviced by an upper-camera processor 124, and the lower three by lower-camera processor 126. The synchronization of the video frames, also controlled by the processors, is coordinated together with the bottle-present photocell pair 54, 56, and produces sync signals that, through a ring counter 142, trigger successive operations of the strobe lights 60. The sync and fault signals of the respective processors are logical OR'ed together to form the inputs to ring counter 142, and to a gate closing driver that operates a solenoid valve (not shown) for feeding air to cylinder 38.

The "reject" and "scratch" status of windows detected by the upper or lower video processors, respectively, can be internally checked within the processors for uniformity for the three angularly-spaced views around the bottle by that processor. In order to check the uniformity between the upper and lower zones, an exclusive-OR arrangement including exclusive-OR gate 132 for the respective "scratch" status signals has its output gated together with the reject signals in order to provide the ultimate reject signal applied to delay mechanism 138, which may be included in a line controller unit, for controlling the reject kicker mechanism. Both the gate operation and kicker are preferably driven by air cylinders, the air supply to the cylinders being controlled by solenoid valves directly responsive to logical signals as shown in FIG. 9. The length of time delay for operation of the kicker can be a set interval determined by the constant speed of the conveyor section at which the inspection system is located. The conveyor section can also be a variable speed unit and the delay inversely-proportionally varied with speed.

It will be appreciated that the use of strobe lights or shutter-operated cameras, multiple cameras, and processing techniques according to the invention is entirely independent of the conveyor speed of the bottles passing through the inspection device. The delay on the kicker, however, must be set to initiate operation of kicker boot 70 upon arrival of the rejected bottle. It may be advisable to determine the delay in operation of the kicker device 70 by sensing the speed of the conveyor. It may also be advisable to shorten the delay slightly more than proportionately required to reflect the added momentum of faster-moving bottles. Sensing allows the conveyor at the inspection device to operate at the variable speed equal to that of the conveyor in the remainder of the system. Such sensing can be accomplished, for example, by timing the pulses from a shaft angle encoder (not shown), or by other known means.

FIGS. 10a through 10c are schematic illustrations showing the video frames, inspection windows and processing steps. As shown in FIG. 10a, the video cameras provide 6 views generally divided into upper and lower views at three angularly-spaced locations. No attempt is made to initially align the bottle label to any particular location, instead the processing of the video signals takes into account the possibility that the label may or may not appear in the image. In FIG. 10b, the placement of the individual inspection window and their relationship to the labels is shown. As shown in FIG. 10b, the inspection windows which would otherwise overlap labels 82, 84, are defined to exclude the labels in the views in which the labels wholly or partly appear.

As shown in FIG. 10c, the correlation of video views is used to determine when diffuseness detected in a scratched bottle is scuffing, and when it indicates a defect. As shown in FIG. 10c, one of the three inspection windows is characterized by scuffing that does not appear at a similar location in the other views. Therefore, the apparent-scuffing in FIG. 10c is found to be dirt.

By means of the foregoing apparatus and method, it is possible to examine a large number of relatively-small video inspection windows in the overall device. The division of the bottle space into angular sections and the two elevation views provide substantial data. At the same time, each window represents a view through the bottle, rather than only the surface of the bottle, being useful to detect features on both the opposite sidewalls. This data can be processed and analyzed at full production speed by means of the gray level processing steps as outlined hereinabove, together resulting in an effective yet inexpensive inspection system especially useful for returnable bottles.

The invention having been disclosed, a number of further embodiments will become apparent to persons skilled in the art. Reference should be made to the appended claims rather than the foregoing specification as indicating the true scope of the invention.

What is claimed is:

1. An inspection system for hollow transparent and translucent bodies, comprising:
   means for delivering the bodies to an inspection zone;
   diffuse illumination means disposed on at least one side of the inspection zone;
   a plurality of video cameras, each of the cameras being on an opposite side of the inspection zone from the diffuse illumination means, and oriented toward and focused on the inspection zone, the cameras being operable to provide a signal representing shades of light and dark of a matrix of pixels in a video field for each of the cameras, the cameras viewing the illumination means through two walls of the bodies, the fields for successive cameras representing sidewall elevation views angularly spaced around the bodies; and,
   at least one digital processor having means for storing a digital representation of said shades of light and dark, the processor being adapted to count occurrences in at least three predetermined ranges of said shades in predetermined areas on the bodies and to determine the number of occurrences of shades in each of said ranges, and the processor being operable to select bodies meeting acceptable criteria based upon said number of occurrences and based upon a correlation of numbers of occurrences for the predetermined areas.

2. The inspection system of claim 1, wherein the ranges of light and dark are chosen to represent clear, opaque, and scuffed bodies.

3. The inspection system of claim 1, wherein the plurality of video cameras directed toward the inspection zone are adapted to record views angularly spaced and spaced in elevation including upper and lower sidewall elevation views from three angles around said bodies.

4. The inspection system of claim 1, wherein the plurality of video cameras are directed toward inspection zones along a path of the conveyor, the cameras being oriented along parallel axes, and further comprising means for turning the bodies disposed between said inspection zones.

5. The inspection system of claim 1, wherein the means for delivering the bodies is a continuously-moving conveyor operable to carry the bodies through the zone, and the diffuse illumination means include at least one strobe light synchronized with a field sync signal from the video cameras.

6. The inspection system of claim 5, comprising three strobe lights, each of the strobe lights being operable upon a field sync signal from one of three pairs of said video cameras.

7. The inspection system of claim 5, wherein the video cameras and strobe light are operable sequentially to provide a signal representing an image of the bodies at incremental positions in said inspection zone as the bodies are continuously moved along.

8. The inspection system of claim 1, wherein the cameras have shutters and are operable to record instantaneous images upon operation of the shutters.

9. The inspection system of claim 1, further comprising a reject kicker device responsive to a signal from the processor representing an acceptable/unacceptable status of successive ones of the bodies, the kicker device including a memory queue for storing said signal for a plurality of said bodies, a bottle-exit detector operable to advance the memory queue for the successive ones of the bodies, and a removal means operating to remove a next successive one of the bodies in response to said signal for said next successive one.

10. The inspection system of claim 1, further comprising a body separator for spacing the bodies delivered to the zone, a gate means for blocking delivery of the bodies, and means for determining a current proportion of the bodies meeting the acceptable criteria, the gate means being located upstream of the inspection zone, the gate means being closable upon detection of a predetermined proportion of said bodies meeting the acceptable criteria.

11. The inspection system of claim 10, wherein the body separator includes an auger screw of decreasing pitch and increasing diameter in the delivery direction, and further comprising a jam detector having a limit switch disposed opposite the auger screw, the limit switch being operated by pressure from the auger screw by misaligned bodies.

12. The inspection system of claim 1, wherein the plurality of video cameras includes six video cameras disposed in pairs and wherein said digital processor includes two digital computers, a first of the computers servicing an upper three of said cameras and the other of the computers servicing a lower three of the cameras, and further comprising circuitry coordinating selection criteria between the two computers.

13. The inspection system of claim 12, wherein said coordinating circuitry is operable to discriminate between bodies scratched on an upper surface only, a lower suface only, and both surfaces.

14. The inspection system of claim 10, further comprising circuitry for detecting stoppage on a conveyor downstream of the inspection system, said circuitry being operable to close the gate means.

15. A method for inspecting transparent and translucent bottles and like containers on a continuously-moving conveyor, comprising the steps of:

back-lighting and inspection zone along the conveyor, at least upon arrival of a bottle at the inspection zone;

recording a plurality of instantaneous video images of the bottle around at least 180 degrees of circumference and converting the video images to numeric digital images, each digital image being a numeric representation of shades of light and dark for each pixel in a matrix of pixels;

comparing the represented shades of light and dark for the pixels and locating at least one edge of the bottle in the digital image by finding a line of contrast between said pixels;

defining at least one window in the digital image, the window being a predetermined span of pixels relative to the at least one edge;

counting occurrences of pixels in the window whose numeric representation occurs within each of at least three ranges of said shades of light and dark;

comparing the counted occurrences in each of said at least three ranges to a predetermined standard of acceptability; and, segregating acceptable bottles from unacceptable bottles according to said standard.

16. The method of claim 15, wherein said ranges of light and dark are chosen to represent clear glass, scuffed glass and opaque material.

17. The method of claim 16, wherein said windows are defined to correspond to areas on the bottles typically subject to scuffing.

18. The method of claim 17, wherein said windows are further defined to correspond to at least one of a bottle lip and a bottle base.

19. The method of claim 17, wherein separate standards of acceptability are applied to windows of the bottles representing areas subject to scuffing, and further comprising the step of comparing amounts of apparent scuffing in spaced areas of the bottle, thereby detecting unusual scuffing patterns indicting defects.

20. The method of claim 15, further comprising the step of blocking arrival of the bottles to the inspection zone upon jamming upstream of the inspection zone, jamming downstream of the inspection zone, and upon detection of a number of defects exceeding a predetermined maximum.

* * * * *